US012653478B2

(12) United States Patent
Han et al.

(10) Patent No.: US 12,653,478 B2
(45) Date of Patent: Jun. 16, 2026

(54) APPARATUS FOR DETERMINING PROJECTION ANGLE OF DENTAL PERIAPICAL RADIOGRAPHY AND METHOD OF USING SAME

(71) Applicant: Fangkai Han, Shanghai (CN)

(72) Inventors: Fangkai Han, Shanghai (CN); Jue Li, Shanghai (CN); Zekuan Yu, Shanghai (CN)

(73) Assignee: Fangkai Han, Shanghai (CN)

( * ) Notice: Subject to any disclaimer, the term of this patent is extended or adjusted under 35 U.S.C. 154(b) by 259 days.

(21) Appl. No.: 18/511,195

(22) Filed: Nov. 16, 2023

(65) Prior Publication Data

US 2024/0081762 A1 Mar. 14, 2024

Related U.S. Application Data

(63) Continuation-in-part of application No. PCT/CN2021/094535, filed on May 19, 2021.

(51) Int. Cl.
*A61B 6/51* (2024.01)
*A61B 6/00* (2024.01)

(52) U.S. Cl.
CPC .............. *A61B 6/51* (2024.01); *A61B 6/4429* (2013.01)

(58) Field of Classification Search
CPC ...... A61B 6/4429; A61B 6/51; G03B 42/047; G03B 42/042; G03B 42/04
See application file for complete search history.

(56) References Cited

U.S. PATENT DOCUMENTS 1,451,507 A * 4/1923 Harris ...................... A61B 6/51
33/391
1,917,433 A * 7/1933 Cressler ............... G03B 42/047
378/165
(Continued)

FOREIGN PATENT DOCUMENTS

CN 102325500 A 1/2012
CN 204863254 U 12/2015
(Continued)

OTHER PUBLICATIONS

Translation of CN-208808510 (Year: 2019).*
(Continued)

*Primary Examiner* — David J Makiya
*Assistant Examiner* — Soorena Kefayati
(74) *Attorney, Agent, or Firm* — Fitch, Even, Tabin & Flannery LLP

(57) ABSTRACT

An apparatus for determining a projection angle of dental periapical radiography includes a body, an angle measuring member, an imaging locator and a projection indicator. The body is a circular cylinder, and the angle measuring member is provided on a top or bottom surface of the body. The imaging locator is detachably coupled to the body, and the projection indicator is pivotally coupled to the body. It operates based on a protractor-assisted projection technique and can avoid ambiguities associated with the angle-bisecting projection technique and operating difficulties associated with the paralleling projection technique. Moreover, it can reduce imaging repetitions and can be easily applied to teaching and professional education due to its ease of understanding and implementation.

14 Claims, 5 Drawing Sheets

(56)                    References Cited

U.S. PATENT DOCUMENTS

| | | | | | |
|---|---|---|---|---|---|
| 2,123,210 | A | * | 7/1938 | Schantz | G03B 42/042 |
| | | | | | 378/170 |
| 2,392,109 | A | * | 1/1946 | Vlock | G03B 42/042 |
| | | | | | 378/170 |
| 4,365,162 | A | * | 12/1982 | Jarby | A61B 6/512 |
| | | | | | 378/170 |
| 4,598,416 | A | * | 7/1986 | Donato | A61B 6/4435 |
| | | | | | 378/170 |
| 6,190,042 | B1 | * | 2/2001 | Dove | A61B 6/4435 |
| | | | | | 378/170 |
| 10,765,385 | B1 | * | 9/2020 | Schaller | G03B 42/042 |
| 2007/0001905 | A1 | * | 1/2007 | Eronen | G01S 5/02 |
| | | | | | 342/463 |
| 2010/0195790 | A1 | * | 8/2010 | Machado | A61B 6/512 |
| | | | | | 378/38 |
| 2011/0222666 | A1 | * | 9/2011 | Choi | A61C 19/04 |
| | | | | | 378/170 |
| 2014/0010350 | A1 | * | 1/2014 | De Godzinsky | A61B 6/587 |
| | | | | | 378/62 |
| 2016/0000522 | A1 | * | 1/2016 | Ripoche | A61B 6/51 |
| | | | | | 433/75 |
| 2017/0354384 | A1 | * | 12/2017 | Tian | A61B 6/4085 |
| 2023/0346326 | A1 | * | 11/2023 | Blecher | A61B 6/512 |

FOREIGN PATENT DOCUMENTS

| | | | | |
|---|---|---|---|---|
| CN | 208808510 | U | * | 5/2019 |
| CN | 111803119 | A | | 10/2020 |
| CN | 112155588 | A | | 1/2021 |
| JP | H11197148 | A | | 7/1999 |
| JP | 2017123896 | A | | 7/2017 |
| WO | 2011083932 | A2 | | 7/2011 |
| WO | 2022241668 | A1 | | 11/2022 |

OTHER PUBLICATIONS

WS/T 608-2018; "Basic operation of oral and maxillofacial conventional X-ray practices"; in Chinese with English Translation (47 pages).

ISR and Written Opinion from PCT/CN2021/094535; mailed Feb. 15, 2022; In Chinese with English Translation (12 pages).

CNIPA; First Office Action and Search Report from Application No. CN 202180002190.9; mailed Feb. 28, 2026; in Chinese with English Translation (25 pages).

* cited by examiner

APPARATUS FOR DETERMINING PROJECTION ANGLE OF DENTAL PERIAPICAL RADIOGRAPHY AND METHOD OF USING SAME

RELATED APPLICATIONS

This application is a continuation-in-part (CIP) application claiming benefit of PCT/CN2021/094535 filed on May 19, 2021, the disclosure of which is incorporated herein in its entirety by reference.

FIELD OF THE INVENTION

The present application relates to the field of X-ray radiography of dental periapical films and, in particular, to an apparatus for determining a projection angle of dental periapical radiography and a method of using the apparatus.

DESCRIPTION OF THE PRIOR ART

At present, in the field of oral and maxillofacial radiology, the following two projection techniques are mainly used in dental X-ray periapical radiography: bisecting-angle projection and paralleling projection.

Clinically, bisecting-angle projection is the most commonly used projection technique. Basic Operation of Oral and Maxillofacial Conventional X-Ray Practices, a standard (WS/T 608-2018) of the People's Republic of China (PRC) for the health industry (referred to hereinafter as the "Standard"), specifies that a central X-ray should be perpendicular to an angle bisector between a long axis of a tooth being treated and an image receptor, and should be parallel to a tangent of a proximal surface of the tooth as much as possible. Although this technique is theoretically plausible, distortion and skew are often found in images taken using this technique, because the central X-ray is not projected perpendicular to the tooth's long axis or the image receptor. Instead, the projection is based on the imaginary angle-bisecting line. This tends to lead to inaccuracy as the exact spatial position of the angle-bisecting line is ambiguous and undeterminable. Textbooks and industry standards recommend using body surface features as fiducial markers. Specifically, a) for a maxillary tooth, with a line connecting the upper edge of the external auditory meatus and the tip of the nose being taken as the imaginary line, the central X-ray may pass 1) the tip of the nose in case of a maxillary central incisor; 2) a midpoint of a line segment connecting the tip of the nose and the ala of the nose on the same side in case of a maxillary central or lateral incisor on the side; or 3) the ala of the nose on the same side in case of a maxillary cuspid; and b) for any mandibular tooth, the imaginary line may run 10 mm above the lower edge of the mandible, and the central X-ray may be projected in alignment with the tooth.

However, the body surface features recommended in textbooks and industry standards as fiducial markers for projection direction and angle determination are all patients' facial soft tissues, which differs from individual to individual in terms of their relative positions to teeth. Therefore, this technique will undoubtedly introduce significant errors and uncertainties to clinical imaging.

The periapical paralleling technique, also known as the right-angle technique, long-beam-limiting cone technique, or long focal length paralleling technique, operates by placing an image receptor in parallel to a long axis of a tooth and projecting a central X-ray perpendicular both to the long axis of the tooth and to the image receptor. Theoretically, images taken using this technique have least distortion. In order to ensure parallelism of the film to the long axis of the tooth, the film has to be placed away from the tooth. Moreover, a high voltage and a fast film are used to reduce the time and amount of exposure. However, this method requires the use of necessary supporting tools, considerable time consumption and occupation of a relatively large intra-oral space for the placement of the film. As seen in clinical practice, in most cases, the parallelism of a film to a long axis of a tooth cannot be ensured within the oral cavity due to an inclination of the teeth, the morphology, thickness and other factors of the surrounding soft tissues (the tongue, the floor of the mouth and the palate) and bones (the alveolar bone, the palatal arch), the volume of the oral cavity and difficulties in patient cooperation.

Thus, although guidelines have been provided in textbooks and standards for helping operators determine a direction and angle of projection from a light source, neither of the above conventional projection techniques can achieve reliable determination and both of them suffer from skew and dimensional distortion of the resultant dental periapical images because they both deal with soft tissues of the human body. Therefore, in the current practice, angle determination has to rely on operators' experience. This, however, lacks reproducibility and reliability.

Therefore, those skilled in the art are directing their effort toward developing an apparatus for determining a projection angle of dental periapical radiography and a method of using the apparatus, which can overcome the drawbacks of the prior art.

SUMMARY OF THE INVENTION

It is an object of the present application to provide an apparatus for determining a projection angle of dental periapical radiography, which comprises a body and an angle measuring member, wherein the angle measuring member is attached to the body, and the angle measuring member is configured to be able to measure and indicate an angle.

Optionally, the body may be a cylinder, or part of a cylinder.

Optionally, the angle measuring member may comprise angular graduation lines provided on a surface of the body.

Optionally, the body may be a circular cylinder.

Optionally, the angular graduation lines may be provided on a top or bottom surface of the body.

Optionally, the apparatus may further comprise an imaging locator detachably coupled to the body.

Optionally, the imaging locator may be configured to determine an angular position through the angle measuring member.

Optionally, the imaging locator may comprise a carrier plate for carrying an image receptor.

Optionally, the apparatus may further comprise a projection indicator pivotally coupled to the body.

Optionally, the projection indicator may be configured to determine an angular position through the angle measuring member.

Optionally, the projection indicator may comprise an indicating plate configured to indicate a projection direction of a light source.

It is another object of the present application to provide an apparatus for determining a projection angle of dental periapical radiography, which comprises a body, an angle measuring member, an imaging locator and a projection indicator, wherein the body is a circular cylinder; the angle measuring member is provided on a top or bottom surface of the body; the imaging locator is detachably coupled to the body; and the projection indicator is pivotally coupled to the body.

Optionally, the angle measuring member may comprise angular graduation lines.

Optionally, the body may comprise a circular cylindrical open bore coaxial with the body, wherein the projection indicator comprises a locating post dimensionally matching the open bore, and the locating post is inserted in the open bore and thereby pivotally couples the projection indicator to the body.

Optionally, the imaging locator may comprise a carrier plate, wherein a slot is provided on a surface of the body, and the carrier plate is inserted in the slot and thereby detachably couples the imaging locator to the body.

Optionally, the carrier plate may be oriented in a radial direction of the body.

Optionally, the carrier plate may be oriented along a zero-degree line of the angular graduation lines.

It is yet another object of the present application to provide a method for determining a projection angle of dental periapical radiography, using the apparatus for determining a projection angle of dental periapical radiography as defined above, wherein, the method specifically includes the steps of:

step 1: attaching an image receptor to the imaging locator;

step 2: placing the image receptor together with the imaging locator at a measurement location;

step 3: determining an angular position of the image receptor through the angle measuring member;

step 4: bringing a tooth into contact with the body and determining an angular position of a long axis of the tooth through the angle measuring member;

step 5: calculating an angular position of an angle bisector between the image receptor and the long axis of the tooth; and step 6: adjusting the projection indicator to an angular position perpendicular to the angle bisector, thereby completing the determination of the projection angle.

It is still yet another object of the present application to provide a method for determining a projection angle of dental periapical radiography, using the apparatus for determining a projection angle of dental periapical radiography as defined above, wherein, the method specifically includes the steps of:

step 1: attaching an image receptor to the carrier plate;

step 2: placing the image receptor together with the carrier plate at a measurement location;

step 3: determining an angular position of the image receptor through the angular graduation lines;

step 4: bringing a tooth into contact with the body and determining an angular position of a long axis of the tooth through the angular graduation lines;

step 5: determining an angular position of an angle bisector an angle between the image receptor and the long axis of the tooth; and step 6: adjusting the projection indicator to an angular position perpendicular to the angle bisector, thereby completing the determination of the projection angle.

Optionally, in step 5, the angular position of the angle bisector between the image receptor and the long axis of the tooth may be an angular position of an angle reading of the long axis of the tooth divided by 2.

The present application offers at least the following benefits:

1) Compared with the bisecting-angle projection and paralleling projection techniques, the apparatus provided herein allow more reliable projection angle determination and more accurate dental periapical radiography and can avoid potential hazards in clinical treatment that may arise from image errors.

2) The apparatus provided herein provides increased ease of imaging and can reduce imaging repetitions, effectively reducing patients' unnecessary exposure to the harmful radiation due to such repetitions.

3) Projection methods using the apparatus provided herein can improve the theoretical system of projection technology for periapical imaging in oral and maxillofacial radiography and can be easily applied to professional education.

Below, the concept, structural details and resulting technical effects of this application will be further described with reference to the accompanying drawings to provide a full understanding of the objects, features and effects of the application.

DETAILED DESCRIPTION OF THE PREFERRED EMBODIMENTS

Figure 1:
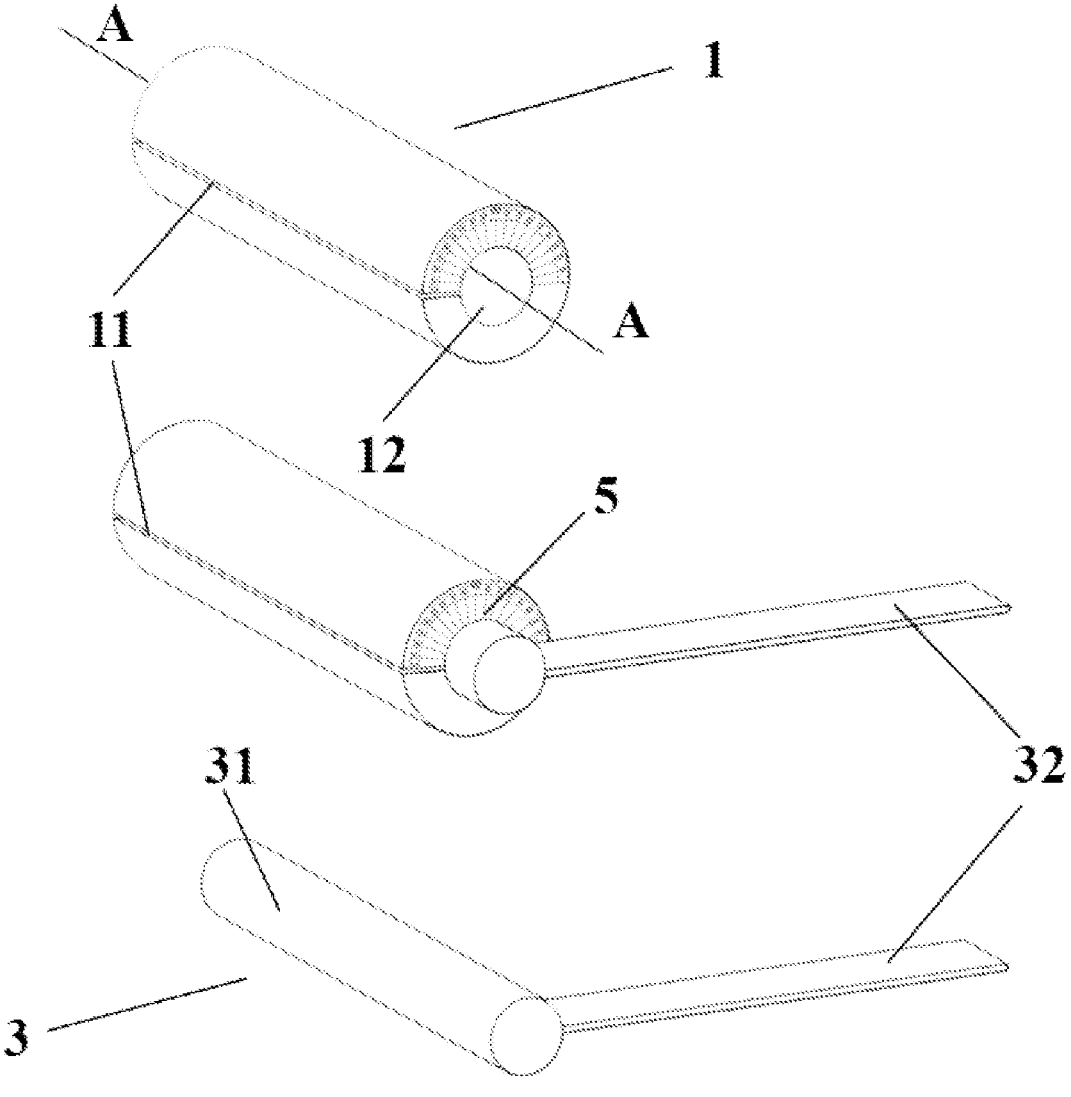
FIG. 1 is a schematic illustration of an embodiment of the present application.

A few preferred embodiments of this application will be described more fully hereinafter with reference to the accompanying drawings so that technical contents thereof will become more apparent and easier to understand. The application can be embodied in various different forms and its scope of protection is in no way limited to the embodiments discussed herein.

Throughout the figures, parts of the same structures are marked with the same reference numerals, and like elements with similar structures or functions are marked with like reference numerals. The dimensions and thickness of each component in the accompanying drawings are arbitrarily shown, and the present application is not limited to any particular dimensions and thickness of each component. Certain parts may be shown somewhat exaggerated in thickness in the interest of clarity.

As used herein, the term "X-ray image receptor" refers to a device that converts an X-ray image into a visible image, either directly or indirectly. Examples include screen-film systems, imaging plates (or films), flat panel detectors, charge-coupled devices, complementary metal-oxide semiconductor devices, etc.

As used herein, the term "dental periapical film" refers to an intraoral dental film for assessing a periapical region of a tooth and the surrounding bones.

Example 1

Figure 2:
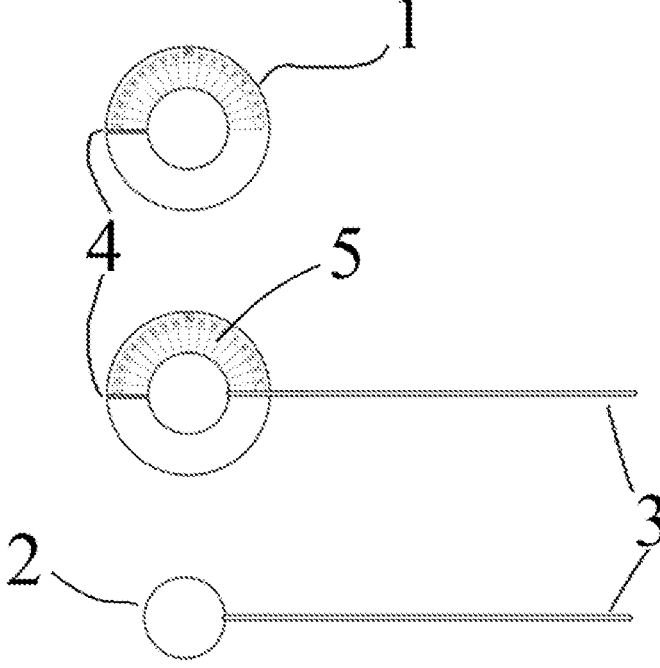
FIG. 2 is a side view of an embodiment of the present application.
Figure 3:
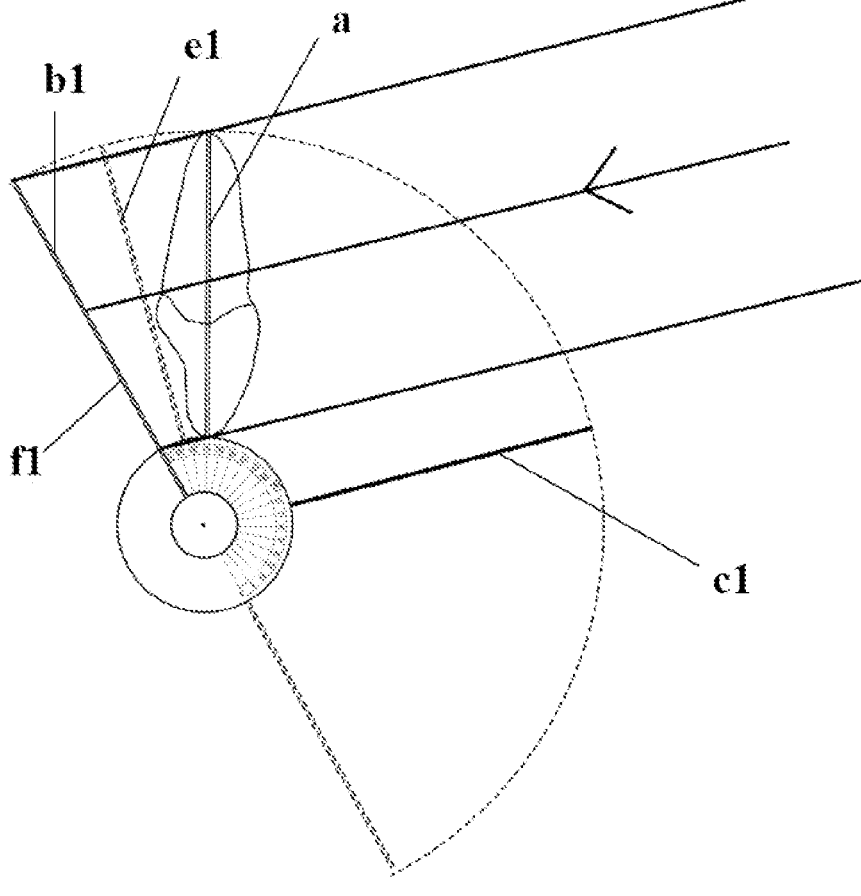
FIG. 3 schematically illustrates operation of an embodiment of the present application.
Figure 4:
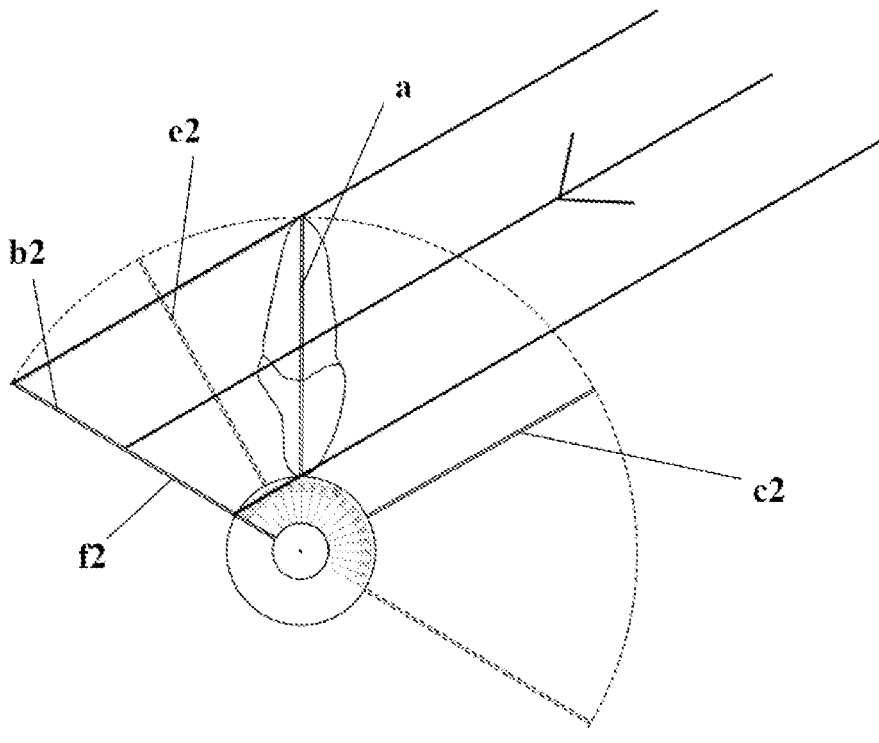
FIG. 4 schematically illustrates operation of an embodiment of the present application.
Figure 5:
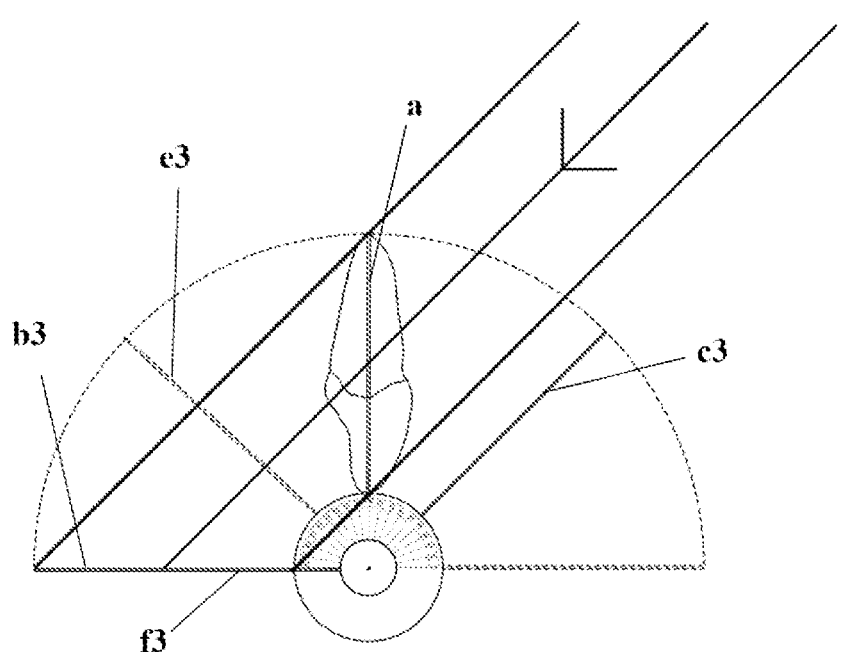
FIG. 5 schematically illustrates operation of an embodiment of the present application.
Figure 6:
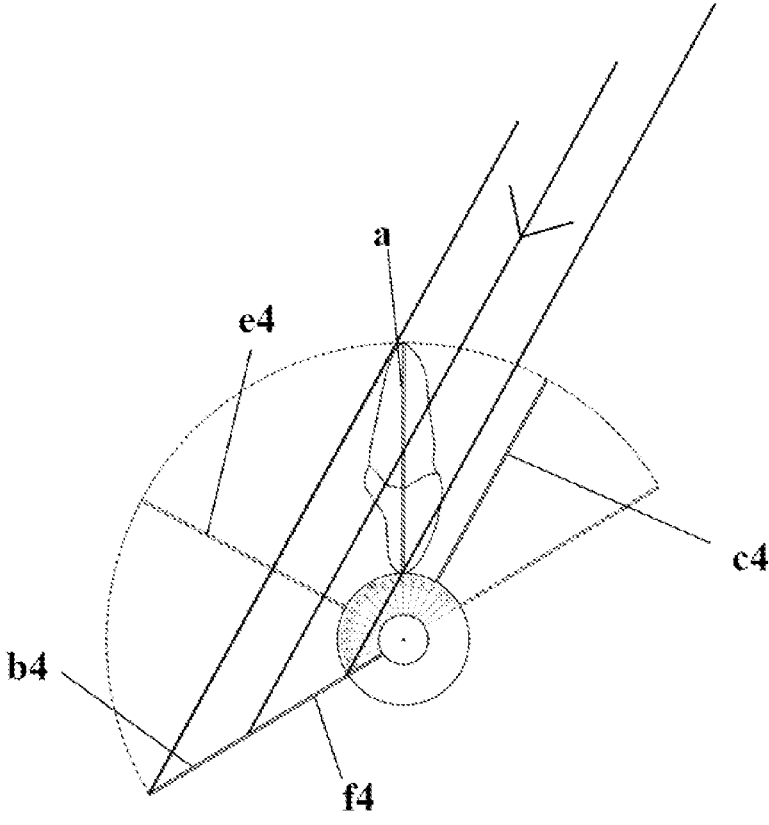
FIG. 6 schematically illustrates operation of an embodiment of the present application.

FIGS. 1 to 2 show an embodiment of the present application. In this embodiment, there is provided an apparatus for determining a projection angle of dental periapical radiography. It includes a body 1 and an angle measuring member 5. The angle measuring member 5 is attached to the body 1 and able to indicate and schedule angular positions of various components of the apparatus. In this embodiment, the body 1 is a cylinder. It is to be noted that, in some embodiments, the body 1 may also be part of a cylinder. For example, it may be a partial cylinder, or a cylinder with a protrusion. However, it is generally cylindrical. Preferably, as shown in FIGS. 1 to 2, the body 1 is a circular cylinder with a circular top and a circular base, which are parallel to each other. The circular cylinder has a radius of 5-7 mm. In FIG. 1, the direction indicated by the axis A defines an axial direction of the circular cylindrical body 1. The radii of the circular top and base define radial directions of the circular cylindrical body 1. In this embodiment, the angle measuring member 5 is preferably implemented as angular graduation lines provided on a surface of the body 1. The angular graduation lines may be provided on a circular cylindrical surface of the body 1. Alternatively, they may be provided on the top or bottom surface of the body 1, as shown in FIG. 1. The angular graduation lines may be drawn on the surface of the body 1, or preformed on a flat or curved graduation plate, for example, in the form of a semi-circular protractor, which is then attached to the body 1 by adhesive bonding, welding or otherwise. In the embodiment, the angular graduation lines preferably indicate 0° to 180°.

This embodiment further includes an imaging locator. The imaging locator is detachably coupled to the body 1, and an angular position of the imaging locator can be determined through the angle measuring member 5. Preferably, the imaging locator includes a carrier plate, which is disposed in a radial direction of the body 1 and used to carry an image receptor. The image receptor is preferred to be an X-ray image receptor. In this embodiment, the body 1 includes a slot 11 extending in the axial direction. A width of the slot 11 matches a thickness of the imaging locator. The imaging locator is inserted into the slot 11 and thereby detachably coupled to the body 1. An angle value indicated by the angular graduation line on the surface of the body 1, along which the imaging locator is oriented, corresponds to the angular position of the imaging locator. In this embodiment, the slot 11, and hence the imaging locator, is preferably provided along the 0- or 180-degree graduation line. In other embodiments, multiple slots 11 may be provided at different positions of the surface of the body 1, and the imaging locator may be inserted in one of the slots.

This embodiment further includes a projection indicator 3. The projection indicator 3 is pivotally coupled to the body 1, and an angular position of the projection indicator 3 can be determined through the angle measuring member 5. In this embodiment, the body 1 includes an open bore 12. The open bore 12 is circular cylindrical and coaxial with the circular cylindrical body 1. The projection indicator 3 includes a locating post 31 dimensionally matching the open bore 12. The locating post 31 is inserted in the open bore 12, thereby pivotally coupling the projection indicator 3 to the body 1. Optionally, both the locating post 31 and the open bore 12 may have a diameter of about 5 mm. The projection indicator 3 further includes an indicating plate 32 fixedly coupled to the locating post 31 along a radial direction. An angle value indicated by the angular graduation line, along which the indicating plate 32 is oriented, corresponds to an angular position of the projection indicator 3. The angular position of the projection indicator 3 varies when it is pivoted about the axis A relative to the body 1. The open bore 12 may extend through the entire body 1, or may be formed by a blind recess in the top or bottom surface of the body 1. Therefore, there may be multiple open bores 12, and the locating post 31 may be inserted into any of the open bores 12 rotatably with respect to the body 1.

In this embodiment, there is also provided a method of using the apparatus as defined above, which includes the steps as follows:

Step 1: Attach the image receptor such as a film or an imaging plate to the carrier plate of the imaging locator.

Step 2: Place the film together with the carrier plate at a measurement location so that a photosensitive surface of the film is in close contact with a side surface of a tooth of interest on the side of the tongue (palate).

Step 3: Determine an angular position of the carrier plate through the angular graduation lines serving as the angle measuring member 5. Since the film is attached to the carrier plate, this is equivalent to determining an angular position of the film.

Step 4: Bring the apex of the tooth of interest into contact with the surface of the body 1 so that a long axis of the tooth is oriented in a radial direction of the body 1. That is, the long axis of the tooth is parallel to one of the angular graduation lines. In this way, an angular position of the long axis of the tooth can be determined through the angular graduation line. In this embodiment, the body 1 is a circular cylinder. Accordingly, through orienting the tooth perpendicular to the circular cylindrical surface, the angular position of the tooth's long axis can be determined.

Step 5: Calculate an angular position of an angle bisector between the film and the long axis of the tooth according to the angular position of the film and the angular position of the long axis of the tooth. In particular, it may be calculated by dividing the sum of the angular position of the film and the angular position of the long axis of the tooth by 2. If the carrier plate is inserted along the 180-degree angular graduation line, as is preferred, its reverse extension passes through the center of the circular cylinder and the 0-degree graduation line. Thus, the position of the angle bisector between the film and the long axis of the tooth can be calculated by dividing the sum of 180° and the angular position of the long axis of the tooth by 2. An angular position of a supplementary angle-bisecting line which is perpendicular to said angle-bisecting line can be calculated by dividing the angular position of the long axis of the tooth by 2.

If the carrier plate is inserted along the 0-degree angular graduation line, as is preferred, its reverse extension passes through the aforementioned center and the 180-degree graduation line. Thus, the position of the angle bisector between the film and the long axis of the tooth can be calculated by dividing the angular position of the long axis of the tooth by 2. An angular position of a supplementary angle-bisecting line which is perpendicular to said angle-bisecting line can be calculated by dividing the sum of 180° and the angular position of the long axis of the tooth by 2.

Step 6: Adjust the indicating plate 32 of the projection indicator 3 to an angular position perpendicular to the angle bisector (i.e., the position of the supplementary angle-bisecting line) to provide a light source with an indication of an angle of projection. This completes the projection angle determination process.

This apparatus is capable of accurately determining a projection angle for a light source, without use of any body surface marker based on facial soft tissue. Therefore, it has low requirements on the operator's experience and operation while providing enhanced reproducibility and reliability of multiple operation cycles.

According to this embodiment, the enhanced projection reproducibility and reliability are based on the protractor-assisted projection technique detailed below.

In FIGS. 3 to 6, the tooth of interest is denoted as a, an image of the tooth as b (obtained at different projection angles and labeled respectively as b1, b2, b3 and b4 in FIGS. 3 to 6), and the angle bisector between the long axis of the tooth and the film as e (labeled respectively as e1, e2, e3 and e4 in FIGS. 3 to 6). As can be readily seen from FIGS. 3 to 6, when an X-ray is projected perpendicular to the angle-bisecting line e, an actual length of the tooth a and its length in the image b define the legs of an isosceles triangle. That is, the actual length of the tooth a is equal to its length in the image b. In order to ensure that the projection direction of the X-ray is perpendicular to the angle-bisecting line, the imaging plate or film is attached to the carrier plate f (labeled respectively as f1, f2, f3 and f4 in FIGS. 3 to 6) in the apparatus, and the angular position of the carrier plate f and hence of the film is determined through the angular graduation lines of the protractor. When the tooth a is brought into contact with the body of the apparatus in such a manner that the long axis of the tooth a passes through the center of the circular cylindrical body, the angular position of the tooth a can be determined through the angular graduation lines of the protractor. Additionally, according to the angular positions of the tooth a and the carrier plate f, the angular position of the angle-bisecting line e and the angular position perpendicular to the angle-bisecting line e can be calculated. Further, the indicating plate c (labeled respectively as c1, c2, c3 and c4 in FIGS. 3 to 6) pivotally coupled to the body of the apparatus can be used to assist in determining the X-ray projection direction by adjusting it to the angular position perpendicular to the angle-bisecting line e (i.e., the angular position of the supplementary angle-bisecting line).

As shown in FIGS. 3 to 6, regardless of the magnitude of the angle between the image b and the tooth a, the light projection direction can be calculated, as long as the angular positions of the tooth a and the image b are determinable through the angular graduation lines.

In this protractor-assisted projection technique for dental periapical radiography, the tooth itself is taken as a reference for determining the projection angle, rather than any virtual marker provided by external facial soft tissue. Moreover, rather than being based on an imaginary angle-bisecting line to adjust the direction of the central X-ray, it achieve accurate projection angle determination based on angle measurements by the protractor. The technique allows assessment and consideration directly based on spatial conditions of a tooth. Further, it is applicable to both a single tooth (based on its long axis) and multiple teeth (based on their common center long axis).

1. This innovative protractor-assisted projection technique incorporates various elements of the protractor mechanism and is a quantitative data-based realization of the application of mathematics and geometry in the field of oral and maxillofacial radiography. It combines the scientific principles of protractors with various concepts including concentricity, radius, angle-bisecting line, supplementary angle (adjacent supplementary angle), right angle, straight angle and parallelism, adding important new parametric concepts to the clinical and research applications in the field of oral and maxillofacial imaging technology.

2. The application of the protractor-assisted projection technique features true angle quantification, ensuring that a tooth can be imaged on a dental periapical film in such a manner that an actual length of the tooth is equal to its length in the image and both can be intuitively represented by concentric radii of equal lengths.

3. The protractor-assisted projection technique extends positional and angular relationships between an imaging plate and a tooth from the traditional direct intersection to an intersection on an extension. A 0-degree or 180-degree angular position of the imaging plate may be predetermined to define a reference radius for subsequent pivoting about the intersection as the center of the radius. When the position of the tooth is reached, an angle in the range defined by the protractor to which the long axis of the tooth corresponds is reversely deduced. Through precise adjustment of the projection angle, regardless of the magnitude of the angle between the tooth and the imaging plate, an image reflecting the actual length of the tooth can be always obtained based on concentric radii of equal lengths. The angle bisector between the tooth and the imaging plate can be intuitively located according to the perpendicular relationship of the supplementary angle-bisecting line and the angle-bisecting line. Thus, once the supplementary angle-bisecting line is located, the projection direction can be determined. According to the principles of this concentric protractor, the X-ray projection direction is exactly parallel to the supplementary angle-bisecting line. In this way, the angle bisector between the imaging plate and the long axis of the tooth can be precisely located. These multiple correspondence relationships enable the tooth and the tooth image presented on the imaging plate to have equal lengths.

This protractor-assisted projection technique can avoid ambiguities associated with the conventional angle-bisecting projection technique and operating difficulties associated with the conventional paralleling projection technique. Inaccurate projection will lead to inconsistent image quality, and excessively long or short tooth images will bring potential hazards to clinical treatment. Moreover, imaging repetitions can be reduced, effectively reducing a patient's unnecessary exposure to the harmful radiation due to such repetitions. Further, as accurate projection is achieved according to known principles, which are easy to understand and implement, it can be easily applied to teaching and professional education. Furthermore, it can well supplement the conventional projection techniques and improve the theoretical system of projection technology for periapical imaging in oral and maxillofacial radiography.

Preferred specific embodiments of the present invention have been described in detail above. It is to be understood that, those of ordinary skill in the art can make various modifications and changes based on the concept of the present invention without exerting any creative effort. Accordingly, all the technical solutions that can be obtained by those skilled in the art by logical analysis, inference or limited experimentation in accordance with the concept of the present invention on the basis of the prior art are intended to fall within the protection scope as defined by the claims.

The invention claimed is:

1. An apparatus for determining a projection angle of dental periapical radiography, comprising a body, an angle measuring member and a projection indicator, wherein the angle measuring member is attached to the body, and the angle measuring member is configured to be able to measure and indicate an angle; and wherein the projection indicator is pivotally coupled to the body, and the projection indicator is configured to determine an angular position through the angle measuring member.

2. The apparatus for determining a projection angle of dental periapical radiography according to claim 1, wherein the body is a cylinder, or part of a cylinder.

3. The apparatus for determining a projection angle of dental periapical radiography according to claim 1, further comprising a carrier plate for carrying an image receptor.

4. The apparatus for determining a projection angle of dental periapical radiography according to claim 1, wherein the projection indicator comprises an indicating plate configured to indicate a projection direction of a light source.

5. The apparatus for determining a projection angle of dental periapical radiography according to claim 2, wherein the angle measuring member comprises angular graduation lines provided on a surface of the body.

6. The apparatus for determining a projection angle of dental periapical radiography according to claim 5, wherein the body is a circular cylinder.

7. The apparatus for determining a projection angle of dental periapical radiography according to claim 6, wherein the angular graduation lines are provided on a top or bottom surface of the body.

8. An apparatus for determining a projection angle of dental periapical radiography, comprising a body, an angle measuring member and a projection indicator, wherein the body is a circular cylinder; the angle measuring member is provided on a top or bottom surface of the body; and the projection indicator is pivotally coupled to the body; and wherein the body comprises a circular cylindrical open bore coaxial with the body; the projection indicator comprises a locating post dimensionally matching the open bore; and the locating post is inserted in the open bore and thereby pivotally couples the projection indicator to the body.

9. The apparatus for determining a projection angle of dental periapical radiography according to claim 8, wherein the angle measuring member comprises angular graduation lines.

10. The apparatus for determining a projection angle of dental periapical radiography according to claim 9, further comprising a carrier plate; wherein a slot is provided on a surface of the body; and the carrier plate is inserted in the slot.

11. The apparatus for determining a projection angle of dental periapical radiography according to claim 10, wherein the carrier plate is oriented in a radial direction of the body.

12. The apparatus for determining a projection angle of dental periapical radiography according to claim 11, wherein the carrier plate is oriented along a zero-degree line of the angular graduation lines.

13. A method for determining a projection angle of dental periapical radiography, using the apparatus for determining a projection angle of dental periapical radiography according to claim 12, wherein, the method specifically includes the steps of:

step 1: attaching an image receptor to the carrier plate;

step 2: placing the image receptor together with the carrier plate at a measurement location;

step 3: determining an angular position of the image receptor through the angular graduation lines;

step 4: bringing a tooth into contact with the body and determining an angular position of a long axis of the tooth through the angular graduation lines;

step 5: determining an angular position of an angle bisector between the image receptor and the long axis of the tooth; and step 6: adjusting the projection indicator to an angular position perpendicular to the angle bisector, thereby completing the determination of the projection angle.

14. The method for determining a projection angle of dental periapical radiography according to claim 13, wherein in step 5, the angular position of the angle bisector between the image receptor and the long axis of the tooth is an angular position of an angle reading of the long axis of the tooth divided by 2.

*  *  *  *  *